United States Patent [19]
Wiltrout et al.

[11] Patent Number: 5,126,129
[45] Date of Patent: Jun. 30, 1992

[54] CANCER THERAPY USING INTERLEUKIN-2 AND FLAVONE COMPOUNDS

[75] Inventors: Robert H. Wiltrout, Frederick; Ronald Hornung, Union Bridge, both of Md.

[73] Assignee: The Government of the United States of America as represented by the Secretary of the Department of Health & Human Services, Washington, D.C.

[21] Appl. No.: 649,182

[22] Filed: Feb. 4, 1991

Related U.S. Application Data

[63] Continuation of Ser. No. 197,352, May 23, 1988, abandoned.

[51] Int. Cl.$^5$ .................. A61K 31/35; A61K 45/05
[52] U.S. Cl. .................. 424/85.2; 514/456
[58] Field of Search .................. 514/456; 424/85.2

[56] References Cited

U.S. PATENT DOCUMENTS 4,602,034  7/1986  Briet et al. .................. 514/456

Primary Examiner—S. J. Friedman
Attorney, Agent, or Firm—Birch, Stewart, Kolasch & Birch

[57] ABSTRACT

Treatment of Cancer with Flavones and Interleukin 2.

18 Claims, 1 Drawing Sheet

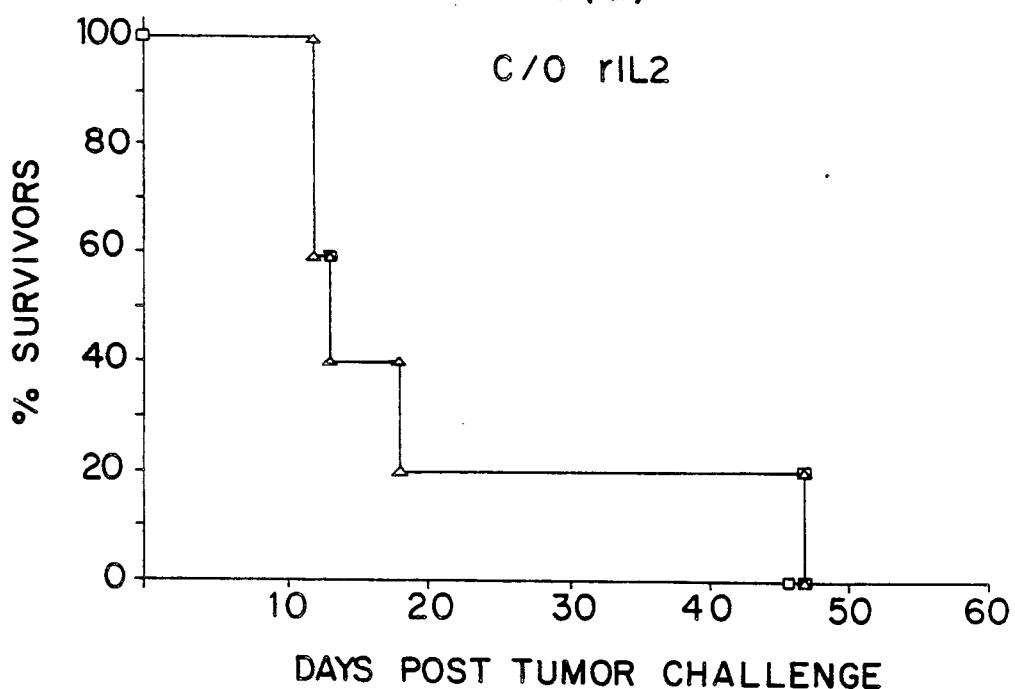
FIG. 1(a) C/O rIL2
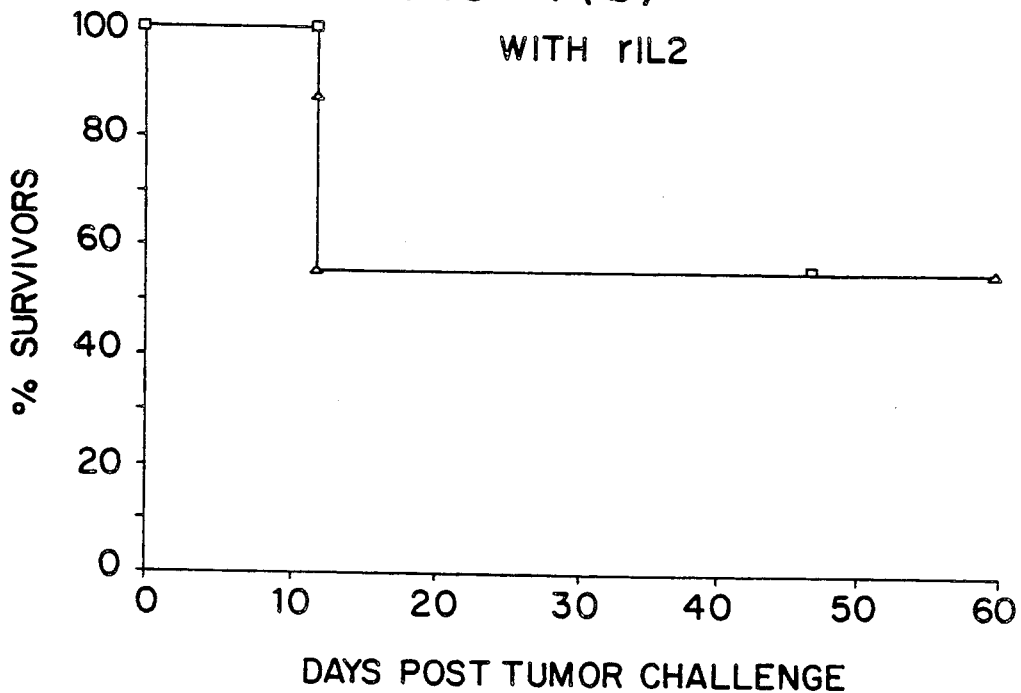
FIG. 1(b) WITH rIL2

CANCER THERAPY USING INTERLEUKIN-2 AND FLAVONE COMPOUNDS

This application is a continuation, of application Ser. No. 07/197,352 filed on May 23, 1988, now abandoned.

FIELD OF THE INVENTION

The present invention relates to a treatment regimen for cancer therapy, and, more particularly, to a treatment regimen for renal carcinoma.

BACKGROUND OF THE INVENTION

Attempts have been made recently to develop immunotherapies for the treatment of cancer based on stimulating the host immune response to the tumor. These approaches were based on attempts to immunize against specific tumor cells or with nonspecific stimulants in the hope that general immune stimulation would concomitantly increase the host antitumor response. Although some experimental evidence indicated that this approach might be feasible in the therapy of established tumors, the inability to stimulate sufficiently strong responses to putative tumor antigens and the general immunoincompetence of the tumor bearing host argued against the success of this approach.

An alternative therapeutic approach to the immunologic treatment of cancer is that of the adoptive transfer of immune cells. Adoptive immunotherapy is defined as the transfer to the tumor-bearing host of active immunologic reagents, such as cells with antitumor reactivity that can mediate, either directly or indirectly, antitumor effects. Adoptive immunotherapy represents an attractive approach to cancer therapy and to other conditions related to immune dysfunction. Because active immunologic reagents are transferred to the host, complete host immunocompetence is not required. Thus, the immunosuppression generally associated with the tumor bearing state does not represent a major problem when using this therapeutic alternative. Since host immunocompetence is not required, and in fact may be beneficial to the effects of the adoptive transfer of immune cells, adoptive immunotherapy can be easily combined with other therapies such as chemotherapy and radiation therapy. Since the transferred reagents are immunologically specific, this treatment modality predicts a high degree of specificity and consequently a low morbidity. Further, in contrast to most other therapies, no immunosuppression is likely to result from this treatment.

A review of previous attempts to perform adoptive immunotherapy for treatment of cancer in animals and humans can be found in Rosenberg et al.; 1977, *Adv. Cancer Res.* 25: 323-388.

Recent studies have demonstrated that the adoptive transfer of specifically immune or broadly cytotoxic lymphocytes generated in the presence of human recombinant interleukin-2 (rIL2) can result in the regression of established tumors in mice and humans. Similarly, the administration of rIL2 alone, in the absence of adoptive immunotherapy, also has been shown to produce some antitumor effects in mice and humans. However, the use of adoptive immunotherapy and rIL2 to treat cancer patients is a complicated, expensive, and toxic form of therapy.

The disadvantage of the use of large amounts of rIL2 either by itself or in combination with adoptive immunotherapy is that such treatment induces a variety of severe and dose-limiting toxic side effects. Therefore, much attention has recently focused on alternative strategies that could exploit the therapeutic benefits of IL-2 while decreasing the expense and logistic difficulties associated with adoptive immunotherapy, as well as decreasing the toxic sequelae associated with high-dose IL-2 therapy.

Renca murine renal cancer has successfully been treated by a therapeutic regimen which combines doxorubin hydrochloride (DOX) and adoptive immunotherapy (AIT) with IL-2, as described in Salup et al., *J. Immunol.*, 138: 641 (1987), and Salup et al., *Cancer Res.*, 46: 3358 (1986). This approach has the advantage of requiring daily administration of a moderate amount of IL-2 rather than the larger amounts required to demonstrate therapeutic effects with IL-2 alone.

Compounds of the formula

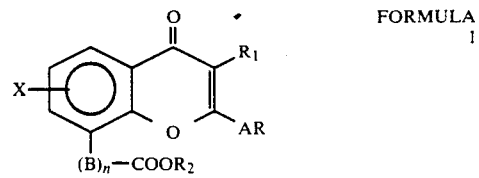

FORMULA 1 in which AR is phenyl substituted by lower alkyl or lower alkoxy, or AR is thienyl, or furyl; $R_1$ is hydrogen; B is a lower linear or branched alkylene or alkenylene radical; X is hydrogen, lower alkyl or lower alkoxy; n equals 1; $R_2$ is hydrogen a lower dialkylamino lower alkyl or morpholinoethyl; or an alkali metal salt of said acid, have been disclosed in U.S. Pat. No. 4,602,234, which is incorporated herein by reference, and in French Patent No. 2,536,397. At the 18th International Leucocyte Culture Conference of June 1987, it was disclosed that the antitumor activity of flavone-8-acetic acid (FAA), a compound disclosed in that patent, was enhanced by administration with interleukin-2.

SUMMARY OF THE INVENTION

It has now been shown that interleukin-2 enhances anticancer activity of Formula 1 analogues of FAA when administered in accord with the method of the invention.

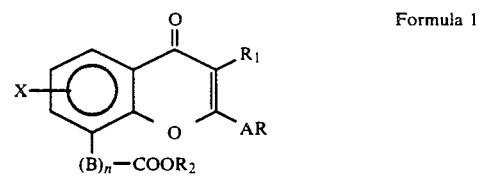

Formula 1

In Formula 1 AR is phenyl substituted by lower alkyl or lower alkoxy, or AR is thienyl, or furyl; $R_1$ is hydrogen; B is a lower linear or branched alkylene or alkenylene radical; X is hydrogen, lower alkyl or lower alkoxy; n equals 1; $R_2$ is hydrogen a lower dialkylamino lower alkyl or morpholinoethyl; or an alkali metal salt of said acid.

It is the object of this invention to provide an improved regimen for treating malignant tumors.

It is another object of this invention to provide an improved method for treating malignant renal tumors.

BRIEF DESCRIPTION OF THE DRAWING

FIG. 1(a) shows effect of treatment with a flavone compound of the formula:

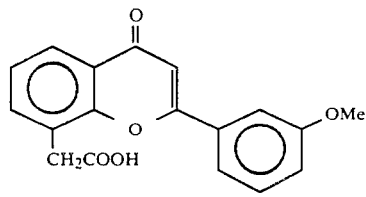

FORMULA 2 alone on survival of Renca-bearing mice.

FIG. 1(b) shows effect of administration of compounds of Formula 2 with rIL2 on survival of Renca-bearing mice.

DETAILED DESCRIPTION OF THE INVENTION

According to the present invention, a treatment regimen for cancer is provided to enhance the effectiveness of interleukin therapy. The preferred methods for administration of flavones of Formula 1 are bolus injection, continuous infusion, or delivery from an osmotic pump in close proximity to the administration of IL-2 by any of the above routes to treat mammals suffering from malignancies. The doses of flavones and IL-2 used and the route of administration and the carriers and/or adjuvants used may vary based on the tumor type being treated and in view of known procedures for treatment of such tumors. The combination of flavones and IL-2 provides synergistic antitumor activity.

The flavones administered were synthesized by the Lyonnaise Industrielle Pharmaceuique.

The rIL2 ($3 \times 10^6$ BRMP units per mg protein), the IL-2 used in the examples, was supplied by Cetus Corporation, Emeryville, Calif.

Polyinosinic-polycytidylic acid and poly-L-lysine stabilized in carboxymethyl cellulose (poly ICLC) was provided by the National Institute of Allergy and Infectious Diseases of Frederick, Md.

All reagents were diluted in Hanks Balanced Salt Solution (HBSS) for administration to the mice.

The tumor model utilized for the present studies is the renca renal adenocarcinoma, a tumor which originated spontaneously and which is maintained by serial transplant in BALC/C mice. The growth characteristics of this tumor have been described in detail in Salup et al., J. Immunol. 138: 641 (1987).

The particular Renca line used for the studies reported hereinafter was isolated from a spontaneous liver metastasis derived from the parental line. Following injection of $1 \times 10^5$ tumor cells under the renal capsule, the solid tumor mass develops rapidly with direct extension to the peritoneal cavity by days 7-9 and metastasis to regional lymph nodes and liver shortly thereafter. Surgical resection of the primary tumor-bearing kidney is potentially curative prior to day 8, but not thereafter, when mice succumb to peritoneal carcinomatosis and subsequent metastatic disease.

The flavone of Formula 2 was administered by injection of 200 mg/kg intravenously and 200 mg/kg intraperitoneally, while 30,000 U. of rIL2 were delivered intraperitoneally. Routinely, the flavone was administered two to four hours after nephrectomy of the primary tumor-bearing kidney on day 11, and rIL2 was administered one time per day for four successive days beginning on the day after nephrectomy and flavone treatment. Statistical analysis of the survival data was performed by the $X^2$ test.

TREATMENT OF MURINE RENAL CANCER BY FLAVONE AND rIL2

FIG. 1 shows the effect of treatment with the flavone of Formula 2 on the survival of Renca-bearing mice. BALB/C mice, 8-10 per group, were injected intrarenally with $1 \times 10_5$ Renca tumor cells on day 0. On day 11, the tumor-bearing kidney was removed and 2-4 hours later 200 mg/kg of the flavone was administered intravenously or intraperitoneally to appropriate groups.

Subsequently, beginning on day 12, some of the flavone pretreated mice were treated with doses of IL-2 at 30,000 U./day for four days. At day 60, all of the mice treated with flavone and IL-2 survived. Of the mice who had received only flavone, all had died by day 50.

These results demonstrate that the use of Formula 1 FAA analogues in association with moderate doses of IL-2 affords appreciably improved long-term survival of mice bearing murine renal cancer as compared to treatment with either a flavone or IL-2 alone.

According to the present invention, the administration of flavones of Formula 1 in association with moderate doses of IL-2 appears to be a more useful approach to the treatment of cancer than administration of high doses of IL-2 alone.

The mechanism by which flavones and rIL2 complement each other in the treatment of cancer is not known. It appears likely that the induction of NK activity, and perhaps the therapeutic effects thereof, are mediated by metabolites of flavones or by cytokines induced by flavones.

The Formula 1 flavones and IL-2 can conveniently be administered intravenously or intraperitoneally, in a suitable carrier.

Carriers which can be used in the present invention include suitable pharmaceutically acceptable carriers comprising excipients and auxiliaries which facilitate processing of the active compounds into preparations which can be used pharmaceutically. Solutions for administration intraperitoneally or intravenously contain from about 0.1 to about 99.5 percent by weight, and preferably from about 25-85 percent by weight, of active ingredient, together with the excipient.

Suitable formulations for parenteral, intraperitoneal, or intravenous administration of the active compounds may include suspensions of the active ingredients as appropriate oily injection suspensions. Suitable lipophilic solvents or vehicles include fatty oils, for example sesame oil, or synthetic fatty acid esters, such as ethyl oleate or triglycerides. Aqueous injection suspensions may contain substances which increase the viscosity of the suspension such as sodium carboxymethylcellulose, sorbitol, or dextran.

The flavones of Formula 1 are preferentially administered by bolus injection, continuous infusion, or delivery from an osmotic pump in close proximity to the administration if rIL2 by any of the above routes. The optimal dose of IL-2 required for use with the flavones of Formula 1 is in the range of about 5,000 to 50,000 u./day, along with about 100 to about 500 mg/kg body weight of the flavone.

The administration of the chosen flavone may commence about one day in advance of or concomitant with the administration of the IL-2. The IL-2 can be administered at least one time per day for at least four days beginning with or after the flavone treatment.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method for treating cancers which are susceptible to treatment with a combination of compounds provided herein, the method comprising administering by injection to a host the combination of:

an effective amount of a flavone compound of the formula:

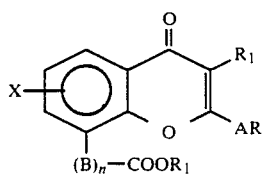

Formula 1 in which AR is phenyl substituted by lower alkyl or lower alkoxy, or AR is thienyl, or furyl; $R_1$ is hydrogen; B is a lower linear or branched alkylene or alkenylene radical; X is hydrogen, lower alkyl or lower alkoxy; n equals 1; $R_2$ is hydrogen, a lower dialkylamino, lower alkyl or morpholinoethyl for treating said cancer; or an alkali metal salt of said acid;

and an effective amount of interleukin 2 for treating said cancer.

2. The method of claim 1 wherein the cancer is renal carcinoma.

3. The method of claim 1 wherein the flavones are administered prior to administration of the interleukin 2.

4. The method of claim 3 wherein the interleukin 2 is administered in at least 4 daily doses.

5. The method of claim 1 wherein the flavones are administered in amounts ranging from about 100 mg/kg body weight to about 500 mg/kg body weight.

6. The method of claim 5 wherein the flavones are administered intravenously.

7. The method of claim 5 wherein the flavones are administered intraperitoneally.

8. The method of claim 1 wherein the treatment agents are administered by a combination of intraperitoneal and intravenous administration.

9. A method of claim 1 wherein the flavone given is a compound of the formula:

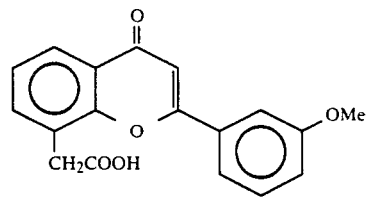

Formula 2 or its sodium salt.

10. A method for treating renal carcinomas, comprising administering by injection to a host an effective amount of a flavone compound of the formula:

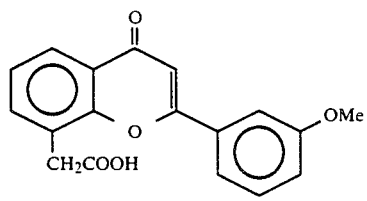

or an alkali metal salt thereof; and an effective amount of interleukin 2.

11. The method of claim 10, wherein the alkali metal salt is the sodium salt.

12. A synergistic pharmaceutical composition for the treatment of cancers which are susceptible to treatment therewith, the composition comprising an effective amount of a flavone compound of the formula:

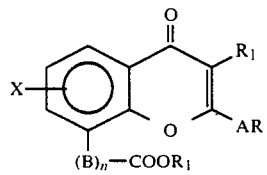

Formula 1 in which AR is phenyl substituted by lower alkyl or lower alkoxy, or AR is thienyl, or furyl; $R_1$ is hydrogen; B is a lower linear or branched alkylene or alkenylene radical; X is hydrogen, lower alkyl or lower alkoxy; n equals 1; $R_2$ is hydrogen, a lower dialkylamino, lower alkyl or morpholinoethyl for treating the cancer; or an alkali metal salt of said acid; and an effective amount of interleukin-2 for treating the cancer; and a pharmaceutically acceptable carrier therefor.

13. The synergistic pharmaceutical composition of claim 12, wherein said flavone compound is

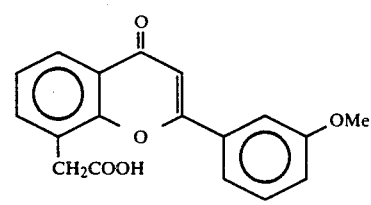

Formula 2 or an alkali metal salt thereof.

14. The synergistic pharmaceutical composition of claim 13, wherein the alkali metal salt is the sodium salt.

15. The method for treating cancers recited in claim 1, wherein:

Ar is phenyl substituted by lower alkyl or lower alkoxy.

16. The method for treating cancers recited in claim 1, wherein:

Ar is phenyl substituted by lower alkyl or lower alkoxy;

X is hydrogen; and $R_2$ is hydrogen.

17. The synergistic pharmaceutical composition recited in claim 12, wherein:

Ar is phenyl substituted by lower alkyl or lower alkoxy.

18. The synergistic pharmaceutical composition recited in claim 12, wherein:

Ar is phenyl substituted by lower alkyl or lower alkoxy;

X is hydrogen; and $R_2$ is hydrogen.

* * * * *